(12) United States Patent
Steinberg et al.

(10) Patent No.: US 7,833,757 B2
(45) Date of Patent: Nov. 16, 2010

(54) METHOD FOR CONDUCTING NON-INVASIVE EARLY DETECTION OF COLON CANCER AND/OR OF COLON CANCER PRECURSOR CELLS

(75) Inventors: Pablo Steinberg, Bergholz-Rehbruecke (DE); Bettina Scholtka, Berlin (DE)

(73) Assignee: Universitael Posidam, Potsdam (DE)

( * ) Notice: Subject to any disclaimer, the term of this patent is extended or adjusted under 35 U.S.C. 154(b) by 630 days.

(21) Appl. No.: 10/573,134

(22) PCT Filed: Sep. 23, 2004

(86) PCT No.: PCT/DE2004/002161

§ 371 (c)(1),
(2), (4) Date: Dec. 18, 2006

(87) PCT Pub. No.: WO2005/030788

PCT Pub. Date: Apr. 7, 2005

(65) Prior Publication Data

US 2007/0172823 A1    Jul. 26, 2007

(30) Foreign Application Priority Data

Sep. 23, 2003    (DE) ................. 103 45 021

(51) Int. Cl.
*C12P 19/34*    (2006.01)
*C07H 21/04*    (2006.01)

(52) U.S. Cl. .................... 435/91.2; 536/24.33

(58) Field of Classification Search ............ None
See application file for complete search history.

(56) References Cited

U.S. PATENT DOCUMENTS

| 6,114,124 | A | * | 9/2000 | Albertsen et al. ............ 435/7.1 |
| 6,586,177 | B1 | | 7/2003 | Shuber |
| 2002/0086386 | A1 | | 7/2002 | Kamb et al. |

FOREIGN PATENT DOCUMENTS

| DE | 197 36 691 A1 | | 2/1999 |
| GB | 2327497 | * | 1/1999 |
| WO | WO 98 58081 | * | 12/1998 |
| WO | 99/04037 | | 1/1999 |
| WO | 01/18252 A2 | | 3/2001 |
| WO | WO 01 18252 | * | 3/2001 |
| WO | WO 01 73002 | * | 10/2001 |

OTHER PUBLICATIONS

Salahshor et al., Colorectal Cancer With and Without Microsatellite Instability Involves Different Genes, Genes, Chromosomes & Cancer 26:247-252 (1999).*
Coste et al., Somatic mutations of the b-catenin gene are frequent in mouse and human hepatocellular carcinomas, Proc. Natl. Acad. Sci. USA vol. 95, pp. 8847-8851, Jul. 1998.*
Nollet et al., Genomic Organization of the Human b-Catenin Gene (CTNNB1),Genomics 32, 413-424 (1996), Article No. 0136.*
Ikawa et al., B-raf, a New Member of the raf Family, Is Activated by DNA Rearrangement, Molecular and Cellular Biology, Jun. 1988, p. 2651-2654 vol. 8, No. 6.*
Davies et al., Mutations of the BRAF gene in human cancer, Nature, vol. 417, Jun. 27, 2002, pp. 949-954.*
Buck et al., Research Report Design Strategies and Performance of Custom DNA Sequencing Primers, BioTechniques vol. 27, No. 3, pp. 528-536, (1999).*
Stratagene, 1998 catalog, p. 39.*
Gerry et al., Universal DNA Microarray Method for Multiplex Detection of Low Abundance Point Mutations, J. Mol. Biol. (1999) 292, 251-262.*
Baba et al., Review, Analysis of disease-causing genes and DNA-based drugs by capillary electrophoresis Towards DNA diagnosis and gene therapy for human diseases, Journal of Chromatography B, 687 (1996) 271-302.*
McCormick, Signalling networks that cause cancer, Trends in Genetics, Millenium issue, 1999, pp. M53- M56.*
Stratagene, 1988 catalog, p. 39.*
Scholtka and Steinberg et al., A gene marker panel covering the Wnt and the Ras-Raf-MEK-MAPK signalling pathways allows to detect gene mutations in 80% of early (UICC I) colon cancer stages in humans, Cancer Epidemiology 33 (2009) 123-129.*
Salahshor Sima et al.; "Colorectal Cancer With and Without Microsatellite Instability Involved Different Genes"; Genes Chromosomes and Cancer; vol. 26, No. 3, Nov. 1999, pp. 247-252.
Rajagopalan H et al.; "RAF/RAS Oncogenes and Mismatch-Repair Status"; Nature, MacMillan Journals Ltd.; London; vol. 418, No. 20, Aug. 2002; p. 934.
Davies H et al.; "Mutations of the BRAF Gene in Human Cancer"; Nature, MacMillan Journals Ltd., London; vol. 417, No. 6892; Jun. 27, 2002, pp. 949-954.
Yuen S T et al.; "Similarity of the Phenotypic Patterns Associated with BRAF and KRAS Mutations in Colorectal Neoplasia"; Cancer Research, American Association for Cancer Research, Baltimore, MD, vol. 62, No. 22, Nov. 15, 2002, pp. 6451-6455.
Prix Lothar et al.; "Diagnostic Biochip Array for Fast and Sensitive Detection of K-ras Mutations in Stool"; Clinical Chemistry; vol. 48, No. 3, Mar. 2002, pp. 428-435.
Dong Seung Myung et al.; "Detecting Colorectal Cancer in Stool With the Use of Multiple Genetic Targets"; Journal of the National Cancer Institute; vol. 93, No. 11, Jun. 6, 2001, pp. 858-865.

* cited by examiner

*Primary Examiner*—Mark Staples
(74) *Attorney, Agent, or Firm*—Bruce S. Londa; Norris McLaughlin & Marcus, PA

(57) ABSTRACT

The invention relates to a method for conducting non-invasive early detection of colon cancer and/or of colon cancer precursor cells, by using primers with which mutation analyses can be carried out in selected regions of genes APC, K-ras, β-catenin and B-raf. The invention also relates to a kit containing said primers, and to the use of these primers and of the kit for analyzing mutations, particularly for conducting the early detection of colon cancer and/or of colon cancer precursory cells.

11 Claims, No Drawings

SEQUENCE LISTING

<160> NUMBER OF SEQ ID NOS: 36

<210> SEQ ID NO 1
<211> LENGTH: 21
<212> TYPE: DNA
<213> ORGANISM: Artificial sequence
<220> FEATURE:
<223> OTHER INFORMATION: Description of the artificial sequence: primer

<400> SEQUENCE: 1
ttgcagttat ggtcaatacc c                                                     21

<210> SEQ ID NO 2
<211> LENGTH: 25
<212> TYPE: DNA
<213> ORGANISM: Artificial sequence
<220> FEATURE:
<223> OTHER INFORMATION: Description of the artificial sequence: primer

<400> SEQUENCE: 2
gtgctctcag tataaacagg ataag                                                 25

<210> SEQ ID NO 3
<211> LENGTH: 20
<212> TYPE: DNA
<213> ORGANISM: Artificial sequence
<220> FEATURE:
<223> OTHER INFORMATION: Description of the artificial sequence: primer

<400> SEQUENCE: 3
cctcaaaagg ctgccacttg                                                       20

<210> SEQ ID NO 4
<211> LENGTH: 23
<212> TYPE: DNA
<213> ORGANISM: Artificial sequence
<220> FEATURE:
<223> OTHER INFORMATION: Description of the artificial sequence: primer

<400> SEQUENCE: 4
ctgtgacact gctggaactt cgc                                                   23

<210> SEQ ID NO 5
<211> LENGTH: 25
<212> TYPE: DNA
<213> ORGANISM: Artificial sequence
<220> FEATURE:
<223> OTHER INFORMATION: Description of the artificial sequence: primer

<400> SEQUENCE: 5
agcaccctag aaccaaatcc agcag                                                 25

<210> SEQ ID NO 6
<211> LENGTH: 20
<212> TYPE: DNA
<213> ORGANISM: Artificial sequence
<220> FEATURE:
<223> OTHER INFORMATION: Description of the artificial sequence: primer

<400> SEQUENCE: 6
tggcatggtt tgtccagggc                                                       20

<210> SEQ ID NO 7
<211> LENGTH: 22

```
<212> TYPE: DNA
<213> ORGANISM: Artificial sequence
<220> FEATURE:
<223> OTHER INFORMATION: Description of the artificial sequence: primer

<400> SEQUENCE: 7
acaaaccatg ccaccaagca ga                                              22

<210> SEQ ID NO 8
<211> LENGTH: 24
<212> TYPE: DNA
<213> ORGANISM: Artificial sequence
<220> FEATURE:
<223> OTHER INFORMATION: Description of the artificial sequence: primer

<400> SEQUENCE: 8
gagcactcag gctggatgaa caag                                            24

<210> SEQ ID NO 9
<211> LENGTH: 20
<212> TYPE: DNA
<213> ORGANISM: Artificial sequence
<220> FEATURE:
<223> OTHER INFORMATION: Description of the artificial sequence: primer

<400> SEQUENCE: 9
ttccagatgc tgatacttta                                                 20

<210> SEQ ID NO 10
<211> LENGTH: 20
<212> TYPE: DNA
<213> ORGANISM: Artificial sequence
<220> FEATURE:
<223> OTHER INFORMATION: Description of the artificial sequence: primer

<400> SEQUENCE: 10
ctgaatcatc taataggtcc                                                 20

<210> SEQ ID NO 11
<211> LENGTH: 21
<212> TYPE: DNA
<213> ORGANISM: Artificial sequence
<220> FEATURE:
<223> OTHER INFORMATION: Description of the artificial sequence: primer

<400> SEQUENCE: 11
ctggtggagt atttgatagt g                                               21

<210> SEQ ID NO 12
<211> LENGTH: 21
<212> TYPE: DNA
<213> ORGANISM: Artificial sequence
<220> FEATURE:
<223> OTHER INFORMATION: Description of the artificial sequence: primer

<400> SEQUENCE: 12
tctattgttg gatcatattc g                                               21

<210> SEQ ID NO 13
<211> LENGTH: 20
<212> TYPE: DNA
<213> ORGANISM: Artificial sequence
<220> FEATURE:
<223> OTHER INFORMATION: Description of the artificial sequence: primer

<400> SEQUENCE: 13
```

-continued

```
ctgatttgat ggagttggac                                          20

<210> SEQ ID NO 14
<211> LENGTH: 20
<212> TYPE: DNA
<213> ORGANISM: Artificial sequence
<220> FEATURE:
<223> OTHER INFORMATION: Description of the artificial sequence: primer

<400> SEQUENCE: 14
cttgagtgaa ggactgagaa                                          20

<210> SEQ ID NO 15
<211> LENGTH: 19
<212> TYPE: DNA
<213> ORGANISM: Artificial sequence
<220> FEATURE:
<223> OTHER INFORMATION: Description of the artificial sequence: primer

<400> SEQUENCE: 15
gaatcagctc catccaagt                                           19

<210> SEQ ID NO 16
<211> LENGTH: 19
<212> TYPE: DNA
<213> ORGANISM: Artificial sequence
<220> FEATURE:
<223> OTHER INFORMATION: Description of the artificial sequence: primer

<400> SEQUENCE: 16
tttctgctat ttgcagggt                                           19

<210> SEQ ID NO 17
<211> LENGTH: 20
<212> TYPE: DNA
<213> ORGANISM: Artificial sequence
<220> FEATURE:
<223> OTHER INFORMATION: Description of the artificial sequence: primer

<400> SEQUENCE: 17
tgtatcacca tctccatatc                                          20

<210> SEQ ID NO 18
<211> LENGTH: 20
<212> TYPE: DNA
<213> ORGANISM: Artificial sequence
<220> FEATURE:
<223> OTHER INFORMATION: Description of the artificial sequence: primer

<400> SEQUENCE: 18
gcattctgat gacttctggt                                          20

<210> SEQ ID NO 19
<211> LENGTH: 21
<212> TYPE: DNA
<213> ORGANISM: Artificial sequence
<220> FEATURE:
<223> OTHER INFORMATION: Description of the artificial sequence: primer
      s for K-ras

<400> SEQUENCE: 19
ctggtggagt atttgatagt g                                        21

<210> SEQ ID NO 20
<211> LENGTH: 21
<212> TYPE: DNA
```

```
<213> ORGANISM: Artificial sequence
<220> FEATURE:
<223> OTHER INFORMATION: Description of the artificial sequence: primer
      as for K-ras

<400> SEQUENCE: 20
tctattgttg gatcatattc g                                              21

<210> SEQ ID NO 21
<211> LENGTH: 20
<212> TYPE: DNA
<213> ORGANISM: Artificial sequence
<220> FEATURE:
<223> OTHER INFORMATION: Description of the artificial sequence: primer
      s for B-Catechin

<400> SEQUENCE: 21
ctgatttgat ggagttggac                                                20

<210> SEQ ID NO 22
<211> LENGTH: 20
<212> TYPE: DNA
<213> ORGANISM: Artificial sequence
<220> FEATURE:
<223> OTHER INFORMATION: Description of the artificial sequence: primer
      as for B-Catechin

<400> SEQUENCE: 22
cttgagtgaa ggactgagaa                                                20

<210> SEQ ID NO 23
<211> LENGTH: 21
<212> TYPE: DNA
<213> ORGANISM: Artificial sequence
<220> FEATURE:
<223> OTHER INFORMATION: Description of the artificial sequence: primer
      s1 for APC

<400> SEQUENCE: 23
ttgcagttat ggtcaatacc c                                              21

<210> SEQ ID NO 24
<211> LENGTH: 25
<212> TYPE: DNA
<213> ORGANISM: Artificial sequence
<220> FEATURE:
<223> OTHER INFORMATION: Description of the artificial sequence: primer
      as1 for APC

<400> SEQUENCE: 24
gtgctctcag tataaacagg ataag                                          25

<210> SEQ ID NO 25
<211> LENGTH: 20
<212> TYPE: DNA
<213> ORGANISM: Artificial sequence
<220> FEATURE:
<223> OTHER INFORMATION: Description of the artificial sequence: primer
      s2 for APC

<400> SEQUENCE: 25
cctcaaaagg ctgccacttg                                                20

<210> SEQ ID NO 26
<211> LENGTH: 23
<212> TYPE: DNA
<213> ORGANISM: Artificial sequence
```

```
<220> FEATURE:
<223> OTHER INFORMATION: Description of the artificial sequence: primer
      as2 for APC

<400> SEQUENCE: 26
ctgtgacact gctggaactt cgc                                              23

<210> SEQ ID NO 27
<211> LENGTH: 25
<212> TYPE: DNA
<213> ORGANISM: Artificial sequence
<220> FEATURE:
<223> OTHER INFORMATION: Description of the artificial sequence: primer
      s3 for APC

<400> SEQUENCE: 27
agcaccctag aaccaaatcc agcag                                            25

<210> SEQ ID NO 28
<211> LENGTH: 20
<212> TYPE: DNA
<213> ORGANISM: Artificial sequence
<220> FEATURE:
<223> OTHER INFORMATION: Description of the artificial sequence: primer
      as3 for APC

<400> SEQUENCE: 28
tggcatggtt tgtccagggc                                                  20

<210> SEQ ID NO 29
<211> LENGTH: 22
<212> TYPE: DNA
<213> ORGANISM: Artificial sequence
<220> FEATURE:
<223> OTHER INFORMATION: Description of the artificial sequence: primer
      s4 for APC

<400> SEQUENCE: 29
acaaaccatg ccaccaagca ga                                               22

<210> SEQ ID NO 30
<211> LENGTH: 24
<212> TYPE: DNA
<213> ORGANISM: Artificial sequence
<220> FEATURE:
<223> OTHER INFORMATION: Description of the artificial sequence: primer
      as4 for APC

<400> SEQUENCE: 30
gagcactcag gctggatgaa caag                                             24

<210> SEQ ID NO 31
<211> LENGTH: 20
<212> TYPE: DNA
<213> ORGANISM: Artificial sequence
<220> FEATURE:
<223> OTHER INFORMATION: Description of the artificial sequence: primer
      s5 for APC

<400> SEQUENCE: 31
ttccagatgc tgatacttta                                                  20
```

<210> SEQ ID NO 32
<211> LENGTH: 20
<212> TYPE: DNA
<213> ORGANISM: Artificial sequence
<220> FEATURE:
<223> OTHER INFORMATION: Description of the artificial sequence: primer
    as5 for APC

<400> SEQUENCE: 32
ctgaatcatc taataggtcc                                         20

<210> SEQ ID NO 33
<211> LENGTH: 19
<212> TYPE: DNA
<213> ORGANISM: Artificial sequence
<220> FEATURE:
<223> OTHER INFORMATION: Description of the artificial sequence: Primer
    alternative s2 for APC

<400> SEQUENCE: 33
gaatcagctc catccaagt                                          19

<210> SEQ ID NO 34
<211> LENGTH: 19
<212> TYPE: DNA
<213> ORGANISM: Artificial sequence
<220> FEATURE:
<223> OTHER INFORMATION: Description of the artificial sequence: Primer
    alternative as2 for APC

<400> SEQUENCE: 34
tttctgctat ttgcagggt                                          19

<210> SEQ ID NO 35
<211> LENGTH: 20
<212> TYPE: DNA
<213> ORGANISM: Artificial sequence
<220> FEATURE:
<223> OTHER INFORMATION: Description of the artificial sequence: Primer
    s for B-raf

<400> SEQUENCE: 35
tgtatcacca tctccatatc                                         20

<210> SEQ ID NO 36
<211> LENGTH: 20
<212> TYPE: DNA
<213> ORGANISM: Artificial sequence
<220> FEATURE:
<223> OTHER INFORMATION: Description of the artificial sequence: Primer
    as for B-raf

<400> SEQUENCE: 36
gcattctgat gacttctggt                                         20

METHOD FOR CONDUCTING NON-INVASIVE EARLY DETECTION OF COLON CANCER AND/OR OF COLON CANCER PRECURSOR CELLS

The invention relates to a method of non-invasive early detection of colon cancer and/or of colon cancer precursor cells, it also relates to primers allowing to perform mutational analyses in selected regions of the genes for APC, K-ras, β-catenin and B-raf in a combined fashion, to a kit comprising said primers, and, in addition, to the use of said primers and said kit in mutational analysis, particularly in early detection of colon cancer and/or colon cancer precursor cells.

Various methods of detecting colon cancer are known in the prior art. The methods of diagnosing colon cancer being most widely used in medicine are hemoccult testing, sigmoidoscopy and coloscopy.

The hemoccult test, which is based on the detection of blood in feces, is not sufficiently specific for the diagnosis of colon cancer due to the diverse possible causes of intestinal hemorrhages. Furthermore, the loss of blood from small colorectal tumors (<2 cm), being 1 to 2 ml per day, is so small that it will not always be detected by this test. Sigmoidoscopy, which is endoscopy of the rectum, is not capable of detecting tumors in the proximal colon. It is estimated that 25 to 34% of colon carcinomas are overlooked when using this method. Coloscopy, which involves endoscopy of the entire colon, detects about 80% of the tumors having a size of $\geqq 1$ cm, but represents an invasive method and, as a consequence, is barely suitable as a regular prophylactic medical examination due to the low acceptance by patients. Therefore, several teams are currently working on the development of methods for the diagnosis of intestinal cancer in fecal samples.

The detection of the carcinoembryonal antigen (CEA) in feces (U.S. Pat. No. 5,741,650 A) is not a reliable test to predict an incipient colon tumor; rather, it is suitable as an indicator for the appearance of relapses. Using a method based on the polymerase chain reaction (PCR), Ahlquist and Shuber have been successful in detecting a similarity of K-ras mutations in samples of feces and tissue from patients with cancer or large adenomas. However, K-ras mutations occur in less than 50% of all colon tumors and are neither present in neoplastic tissue, for which reason this marker alone is not sufficient for a detection method in the early detection of intestinal cancer. The same group has developed a test which detects 15 well-defined point mutations in the genes for K-ras, APC, p53 and Bat-26 and detects "long" DNA in fecal samples. It is intended at present to subject this test to preclinical studies. Due to the large number of mutation sites investigated in this test, the expected sensitivity and specificity are very high, but indeed, this is an extremely cost-intensive test.

Previous tests for the determination of mutations triggering intestinal cancer do not allow reliable detection when using samples obtained by merely non-invasive means, especially samples of feces. The prior art discloses primer sequences used to detect individual mutations. When used in combination in feces, reliable detection of multiple mutations is not possible as a result of undesirable interactions with feces and among each other. In particular, the numerous components of the intestinal flora "mask" the primers in such a way that the latter no longer bind to their targets. Given a combination of primers, well-known methods therefore use isolated cells from feces instead of directly using the latter. Furthermore, samples of feces also comprise wild-type and mutated DNAs, consequently making direct sequencing of PCR products impossible.

The prior art also describes a test system for the detection of cancerous diseases, wherein detection of an antiapoptotic member of the Bcl-2 family is used in combination with a member of the Raf family. In this case, however, both markers must be present in the same sample, the samples being transgenic non-human mammals or isolated human or non-human cells. The above test systems cannot be used with human feces sample material.

Furthermore, the prior art discloses the combination of B-raf genes and their use in the detection of tumors. Here, the mutants are isolated from a human primary tumor which has to be removed by means of invasive surgery. Thereafter, a polypeptide is isolated therefrom. Also, healthy control tissue from the patient must be collected. This method does not allow detection of early mutations. This method neither allows investigation on fecal samples, but only on detected and isolated complete tumor cells, from which polypeptides are preferably isolated. Further, this method is restricted to well-defined point mutations, so that mutations such as insertions, deletions or other cannot be detected within a confined sequence region. Possible combinations with other genes are neither disclosed nor made obvious.

Furthermore, methods allowing detection of circulating cancer cells in body fluids are known. Without isolating and detecting complete tumor cells, none of the above methods is usable as diagnostic procedure.

Screening methods for therapeutic agents modifying the β-catenin signal pathway have also been described. To this end, probes are used, i.e., the so-called cadherin "perturbagen". The disclosed sequences hybridize with cadherin, which is a β-catenin-binding protein, but not with β-catenin itself.

Further methods are known in the prior art, wherein the DNA integrity and the DNA quantity for selected genes, e.g. for K-ras and APC, is determined and correlated with standards or threshold values. However, these methods neither disclose mutational analysis, nor primer sequences that would be particularly advantageous. A common feature of these methods is that no mutational analysis is performed, e.g. using an automatable electrophoretic procedure such as SSCP.

In addition, methods are known wherein tissues from intramucosal lesions or colon tumors are isolated from azoxymethane-treated rats by means of laser microdissection. DNA is isolated from said lesions and tumors, portions of exon 3 of the β-catenin gene and of exon 1 of the K-ras gene are amplified and directly sequenced using mutational analysis. However, such methods cannot be used with samples of feces because fecal samples contain a mixture of wild-type and mutated DNA. As a consequence, direct sequencing of the PCR products is not possible in such methods.

The object of the invention was therefore to provide a method that would allow easy, reliable and effective detection of colon cancer or colon cancer precursor cells in a sample of feces, avoiding the disadvantages of the prior art, particularly undesirable interaction of primers with each other and with a fecal sample.

The invention solves the above problem by providing a method for the non-invasive early detection of colon cancer and/or intestinal cancer precursor cells by means of mutational analysis of the genes for APC, K-ras, β-catenin and B-raf in a sample, said method comprising the following steps:

collecting a stool and/or tissue sample,
homogenizing the sample,
obtaining DNA from the sample, performing an amplification reaction, preferably a PCR reaction, in the genes for APC, K-ras, β-catenin and B-raf, using the primers identified as

```
s1  (SEQ ID NO. 1)
TTGCAGTTATGGTCAATACCC as1 (SEQ ID NO. 2)
GTGCTCTCAGTATAAACAGGATAAG s2  (SEQ ID NO. 3)
CCTCAAAAGGCTGCCACTTG as2 (SEQ ID NO. 4)
CTGTGACACTGCTGGAACTTCGC s3  (SEQ ID NO. 5)
AGCACCCTAGAACCAAATCCAGCAG as3 (SEQ ID NO. 6)
TGGCATGGTTTGTCCAGGGC s4  (SEQ ID NO. 7)
ACAAACCATGCCACCAAGCAGA as4 (SEQ ID NO. 8)
GAGCACTCAGGCTGGATGAACAAG s5  (SEQ ID NO. 9)
TTCCAGATGCTGATACTTTA as5 (SEQ ID NO. 10)
CTGAATCATCTAATAGGTCC for APC, the primers
s   (SEQ ID NO. 11)
CTGGTGGAGTATTTGATAGTG as  (SEQ ID NO. 12)
TCTATTGTTGGATCATATTC for K-ras, the primers
s   (SEQ ID NO. 13)
CTGATTTGATGGAGTTGGAC as  (SEQ ID NO. 14)
CTTGAGTGAAGGACTGAGA for β-catenin, and/or the primers
s   (SEQ ID NO. 17)
TGTATCACCATCTCCATATC as  (SEQ ID NO. 18)
GCATTCTGATGACTTCTGGT
``` for B-raf, wherein amplification products are formed, and performing a mutational analysis in the amplification products.

Alternatively,

```
s2  (SEQ ID NO. 15):
GAATCAGCTCCATCCAAGT as2 (SEQ ID NO. 16):
``` can be used as primer pair as/as2 for human APC in said method or in a kit.

Surprisingly, the above combined method allows noninvasive, inexpensive and easy detection of colon cancer and/or colon cancer precursor cells at a very early stage with higher reliability and effectiveness, saving time, material and operating steps, as well as saving cost and fine chemicals difficult to obtain. Furthermore, the inventive combination of process steps expands the technical options of cancer diagnostics, thus providing another way of colon cancer early detection.

Advantageously, the small number of operating steps enables optional automation or miniaturization of this method.

Furthermore, the method according to the invention combines the advantages of easy sample collection and the option of diagnosing developing colon cancer or colon cancer precursor cells at an early stage. Being a non-invasive method, in which e.g. delivering a sample of feces or, if necessary, a tissue sample is sufficient, the method achieves high acceptance among subjects, which subjects can be humans or animals, for example. Therefore, the method can be used in routine tests, but also in prophylactic medical examinations. Owing to the combination of the three investigated genes for APC, K-ras and β-catenin and/or B-raf which is used, thus being correlated with early mutation results during colon cancerogenesis, it is possible to achieve higher sensitivity and specificity compared to well-known tests which, in particular, are limited to mutation of a single gene. Advantageously, the method of the invention is not confined to a few well-defined point mutations; rather, the method optionally allows detection of previously unknown mutations within regions where mutations occur more frequently in genes under investigation.

Since different types of colon cancer involve different pathways of cancerogenesis, one problem in the development of a diagnostic kit was to combine suitable markers detecting, as comprehensively as possible, all types or many types of colon carcinomas, also including spontaneous colon carcinomas with and without microsatellite instability, which can be induced by a variety of stimuli such as nutrition, frequent consumption of alcohol or tobacco, exposure to physical or chemical influences, etc.

The selected combination of the above-mentioned four genes in combination with the claimed primers allows easy, reliable and effective diagnosis of colon cancer.

Surprisingly, it has thus been possible to demonstrate that the combination of detecting by means of primers selected in a well-defined fashion allows non-invasive early detection of colon cancer and/or colon cancer precursor cells.

In the method according to the invention, wherein five process steps take effect concurrently, amplification reactions are performed in four genes using selected markers. The individual amplification reactions and the five individual steps of the process take effect concurrently to achieve the technical overall success of non-invasive early detection of colon cancer and/or colon cancer precursor cells in the investigated sample. As a result of the functional dependence of the individual process steps and amplification reactions, the technical overall success of cancer early detection is possible. In the meaning of a combination invention, the individual process steps neither have to be interdependent nor require simultaneous performing. The individual process steps, particularly the individual amplification reactions, do not furnish an isolated single result; rather, as a result of the combination concept of the teaching according to the present application, the individual process steps are combined into the integrated objective of reliable non-invasive early detection in a sample of feces. Such a reliable technical statement would not be possible when using the individual, noncombined process steps. Single determination of individual mutational analyses does not allow any reliable statement as to the presence of early-stage colon cancer cells or colon cancer precursor cells in a sample of feces. The results of the individual process steps and, in particular, of the individual amplification reactions, can be evaluated and combined using an algorithm, for example, so that statements as to the non-invasive early detection are possible. It is only by virtue of said combination that it is possible to make reliable and prompt statements as to colon cancer and/or colon cancer precursor cells in a sample, especially in a sample of feces.

In this method, the tumor markers are combined in such a way that each sample from a patient is analyzed with a total of four markers, namely, each time with two markers, alternatively mutated in case of a cancerous disease, from at least two different biochemical signal pathways associated with cell proliferation or tumor growth. In the present case, markers are the genes under investigation. Optionally, several sections can thus be analyzed from a marker gene. The signal pathways covered by the markers integrated in this method are the wnt signal pathway and the MAPK signal pathway. Components of the method are the markers APC, on the one hand, and β-catenin, on the other hand, from the wnt signal pathway, together with the markers K-ras, on the one hand, and B-raf, on the other hand, from the MAPK signal pathway. This combination of two markers from the wnt signal pathway, together with the two markers from the MAPK signal pathway, allows reliable diagnosis of colon carcinoma. Using this combination, it is even possible to achieve a sensitivity in non-invasive colon carcinoma diagnostics which is comparable to that of coloscopy. Moreover, and advantageously, these are markers undergoing mutation at an early point in time during colon cancerogenesis.

By virtue of the teaching according to the invention, mutations in genes related to two signal pathways are advantageously detected: to allow each cell of the human body to respond to exterior signals or signals from other cells, such signals must be recognized, processed and passed further on. This is effected via intracellular signal pathways. A signal pathway begins with the arrival of a signal, e.g. a hormone or a neurotransmitter, at the cell surface. The signal molecule binds to cellular proteins, i.e., the receptors, which are activated thereby, triggering a cascade inside the cell, during the course of which further proteins are activated. At the same time, the triggering signal is amplified. At the end of the cascade or of the signal pathway, either enzymes are present which have an important function in the metabolism, or transcription factors which regulate gene expression. These signal pathways regulate the metabolism, growth and cell division, for example. The merit of the inventors lies in the discovery that the tumor probability can be determined reliably and in a non-invasive fashion by analyzing the wnt signal pathway, which regulates cell adhesion and cell migration, and the MAPK signal pathway, which controls cell division and cell development. Mutations in the genes involved result in misregulation of the above intracellular signal pathways, e.g. in complete loss of function of a signal pathway component or even in permanent activation and, as a consequence, formation of a tumor.

It is a well-known fact that the APC gene is frequently mutated in colorectal carcinoma. The gene product is a shortened protein which is no longer capable of regulating the amount of β-catenin protein present in the cell. In a complex with the TCF transcription factor, β-catenin subsequently launches the gene expression of target genes, with the consequence of uncontrolled cell proliferation. Alternatively, the β-catenin gene can be activated constitutively by mutation. In tumor cells, however, it is invariably either APC or β-catenin that is mutated, but not both at the same time. This makes sense because the two alternative mutations have the same effect because the respective gene products occur in the same intracellular signal pathway, i.e., the wnt signal pathway.

The situation in the MAPK signal pathway is comparable. Similarly, the components K-ras and B-raf are alternatively mutated in colorectal carcinoma, thereby being constitutively activated. In this case as well, the consequence is uncontrolled cell division and, as a result, tumor formation.

The combination of alternatively mutated markers APC, β-catenin, k-ras and B-raf diagnostically covers two signal pathways contributing to tumor formation, and said combination of markers allows non-invasive detection of tumors with very high sensitivity and at a very early point in time.

As a result of combining the two signal pathways or mutually excluding gene mutations from the above-mentioned two signal pathways in a single test, it is possible with advantage to reliably detect most tumors because at least one of the above-mentioned two signal pathways is involved during their formation, with the consequence of impaired cell-cell adhesion or increased transcription of genes inducing cell growth or cell division. The above composition of the spectrum of tumor markers, which is used in the test method according to the invention and takes into account the signal pathways in the cell important for tumor formation by using mutually excluding mutations as markers each time, is different from other previous tests wherein as many markers as possible, which frequently undergo mutation in colorectal carcinoma, are simply integrated in a test.

Obviously, other pairs of gene mutations which are mutually excluded or alternatively present in colorectal carcinomas and occur in other common signal pathways can be integrated as markers in this method or in a test allowing implementation thereof.

Advantageously, it is also possible to detect previously unknown mutations in the selected sequence sections.

For example, the method according to the invention can be performed in such a way that a pea-sized portion is removed from excreted human feces and subsequently shock-frozen in liquid nitrogen. Of course, it is also possible to use human tumor tissue or precursors thereof, such as aberrant crypts, adenomas or adenocarcinomas collected during a biopsy, e.g. in the course of a coloscopy or during a surgery. Therafter, the sample of feces or tissue sample can be homogenized, and this can be done e.g. in buffer systems using kits well-known to those skilled in the art. Subsequently, the samples thus homogenized are centrifuged so as to allow isolation of DNA from the supernatant of the sample homogenate. Optionally, the step of isolating the DNA can be preceded by accumulation thereof. For example, this can be effected in such a way that target genes are obtained from the total DNA by hybridizing sequence-specific biotinylated oligonucleotides with the target genes for APC, K-ras, β-catenin and B-raf and coupling the biotin residue to streptavidin, followed by separation via magnetic particles using kits well-known to those skilled in the art. The oligonucleotide sequences must be selected in such a way that the sequences hybridize with regions flanked by the primers subsequently used or situated close to the amplified section.

Preferably, it is also possible to effect accumulation by excluding fragmented DNA with a size of <200 bp which is characteristic for DNA from apoptotic cells. In this way, neoplastic "long" DNA is separated. Subsequently, another amplification reaction can be performed using primers sequence-specific to selected regions in the genes for APC, K-ras, β-catenin and B-raf. For APC, the primer pairs are selected so as to allow amplification of overlapping sequences in exon 15 within the well-known region of frequently occurring mutations (mutational cluster region; MCR). For β-catenin, the primers are situated on both sides of the MCR located in exon 3, and for K-ras, the primers are situated on both sides of the well-known MCR located in exon 1. All primers are selected in such a way that the PCR products would have a size of from 180 to 350 bp. The following primer sequences are employed, each one in 51'→3' direction:

SEQ ID NO. 11
SEQ ID NO. 12

β-catenin
SEQ ID NO. 13
SEQ ID NO. 14

APC
SEQ ID NO. 1
SEQ ID NO. 2
SEQ ID NO. 3
SEQ ID NO. 4
SEQ ID NO. 5
SEQ ID NO. 6
SEQ ID NO. 7
SEQ ID NO. 8
SEQ ID NO. 9
SEQ ID NO. 10 or alternatively:
SEQ ID NO. 15
SEQ ID NO. 16

B-raf
SEQ ID NO. 17
SEQ ID NO. 18

Preferably, it is possible in the further course of the procedure to investigate the PCR products obtained with said primers, using an agarose gel. However, purification of the PCR products can also be effected by means of a kit well-known to those skilled in the art, without checking the PCR products in an agarose gel. For mutational analysis of the PCR products, a number of well-known methods are available to a person skilled in the art, such as electrophoretic techniques, preferably single-stranded conformation polymorphism analysis (SSCP).

Using SSCP analysis, rapid and easy detection of polymorphisms and mutations in DNA single strands is possible in a preferred fashion, utilizing the fact that the single strands under non-denaturing gel conditions are not linear, but are present in a folded state as a result of intramolecular base pairing. One single base substitution per strand is sufficient to cause deviating migration behavior. With fragments having a length of 200 bp, the specificity should be close to 100%. Migration time, performance, crosslinking and acrylamide concentration can be optimized individually for different DNA sections, using routine tests. Glycerol can be admixed to improve separation of the single strands.

Here, the conformation of single strands of samples compared to the wild-type standard can be detected. It can make sense in some cases to effect DNA extraction from the SSCP gel and sequencing of the DNA thus extracted or of the corresponding PCR products in order to specifically detect particular mutations. Other methods of mutational analysis are DHPLC and DNA chip technology.

The detection of mutations thus performed, wherein the genes for APC, K-ras, β-catenin and B-raf are employed as markers, is advantageous because in this way, all types of spontaneous colon carcinomas can be detected at a particularly early point in time, because a high percentage of K-ras or β-catenin is mutated in tumor precursors, aberrant crypts and adenomas, and either APC or β-catenin is mutated in adenomas and early adenocarcinomas.

Consequently, not only a few well-known mutations can be detected with the method according to the invention, but rather, all point mutations—optionally including unknown mutations—within gene sections known for especially frequently occurring mutations will be detected. For example, this method is superior to immunologic detection of proteins truncated as a result of mutation. It is especially the K-ras/B-raf pair within the combination according to the invention that allows particularly reliable diagnosis, because the MAPK signal pathway is diagnostically covered by said markers.

Obviously, the detection of mutations in selected sections of the genes for APC, K-ras, β-catenin and B-raf can be effected, in particular, by means of a DNA chip, said DNA chip including probes for APC, K-ras, β-catenin and B-raf from those regions of the above-mentioned genes that are flanked by the above-mentioned primer sequences. The term "bordered or flanked by primer sequences" means that the DNA chip technology does not necessarily require the use of conventional PCR primers amplifying a DNA strand of a length determined by the position of the two primers (sense and antisense). In the event of a conventional PCR, the PCR product is bordered or flanked by the primers. In contrast, DNA chips frequently use single oligonucleotides as probes, which hybridize with the sample DNA, and the probe may include a defined point mutation, for example. The chip may include the above-mentioned primers as probes, but also other probes hybridizing with other sections of the products from PCR reactions with the above-mentioned primers.

The invention also relates to primer sequences selected from the group comprising:

```
the primers
TTGCAGTTATGGTCAATACCC,       SEQ ID NO. 1

GTGCTCTCAGTATAAACAGGATAAG,   SEQ ID NO. 2

CCTCAAAAGGCTGCCACTTG,        SEQ ID NO. 3

CTGTGACACTGCTGGAACTTCGC,     SEQ ID NO. 4

AGCACCCTAGAACCAAATCCAGCAG,   SEQ ID NO. 5

TGGCATGGTTTGTCCAGGGC,        SEQ ID NO. 6

ACAAACCATGCCACCAAGCAGA,      SEQ ID NO. 7

GAGCACTCAGGCTGGATGAACAAG,    SEQ ID NO. 8

TTCCAGATGCTGATACTTTA,        SEQ ID NO. 9

CTGAATCATCTAATAGGTCC,        SEQ ID NO. 10

CTGGTGGAGTATTTGATAGTG,       SEQ ID NO. 11

TCTATTGTTGGATCATATTCG,       SEQ ID NO. 12

CTGATTTGATGGAGTTGGAC,        SEQ ID NO. 13

CTTGAGTGAAGGACTGAGAA,        SEQ ID NO. 14

GAATCAGCTCCATCCAAGT,         SEQ ID NO. 15

TTTCTGCTATTTGCAGGGT,         SEQ ID NO. 16

TGTATCACCATCTCCATATC,        SEQ ID NO. 17

GCATTCTGATGACTTCTGGT,        SEQ ID NO. 18
``` the sequences
SEQ ID NO. 11
SEQ ID NO. 12 being used for K-ras, the sequences
SEQ ID NO. 13
SEQ ID NO. 14 being used for β-catenin, the sequences

SEQ ID NO. 1
SEQ ID NO. 2
SEQ ID NO. 3
SEQ ID NO. 4
SEQ ID NO. 5
SEQ ID NO. 6
SEQ ID NO. 7
SEQ ID NO. 8
SEQ ID NO. 9
SEQ ID NO. 10 or alternatively,

SEQ ID NO. 15
SEQ ID NO. 16 being used for APC, and the sequences

SEQ ID NO. 17
SEQ ID NO. 18 being used for B-raf.

The primers can be used with advantage in the diagnosis of colon cancer and/or colon cancer precursor cells.

The method uses primer sequences having sufficient homology to the regions on the genes for APC, K-ras, β-catenin and B-raf specified below to form an amplification product by polymerase chain reaction:

| Designation of gene | GeneBank (NIH, USA) | Primer position |
|---|---|---|
| APC | NM 000038 | SEQ ID NO. 1: 3020-3040 |
| | | SEQ ID NO. 2: 3283-3259 |
| | | SEQ ID NO. 3: 3765-3784 |
| | | SEQ ID NO. 4: 4022-4000 |
| | | SEQ ID NO. 5: 4021-4045 |
| | | SEQ ID NO. 6: 4334-4315 |
| | | SEQ ID NO. 7: 4322-4343 |
| | | SEQ ID NO. 8: 4563-4540 |
| | | SEQ ID NO. 9: 4483-4502 |
| | | SEQ ID NO. 10: 4740-4721 |
| (alternatively) | | SEQ ID NO. 15: 3722-3740 |
| | | SEQ ID NO. 16: 3957-3939 |
| β-Catenin | NM 001904 | SEQ ID NO. 13: 228-247 |
| | | SEQ ID NO. 14: 443-424 |
| K-ras | L 00045 | SEQ ID NO. 11: 4-24 |
| | | SEQ ID NO. 12: 205-185 |
| B-raf | M 95712 | fw: 1671-1690 |
| | | rev: 1924-1943 |

The invention also relates to a kit comprising said primers, and to the use of said kit in non-invasive early detection of colon cancer and/or colon cancer precursor cells. The kit may optionally include information relating to combining the contents of the kit. The kit may also comprise additional chemical reagents required in the detection of colon cancer. Furthermore, the kit may comprise adjuvants, vehicles, enzymes, marker substances, as well as storage containers, microscopic slides, optical instruments, or other device components allowing or supporting biological, chemical and/or physical determination of colon cancer or colon cancer precursor cells.

Without intending to be limiting, the invention will be explained in more detail with reference to the following example.

EXAMPLE a) Collection of fecal sample or tissue sample

Human feces: collect a pea-sized portion of excreted feces with collecting spoon, transfer into a commercial feces tube, shock-freeze in liquid nitrogen, store at −80° C.;

Rodent feces: scrape out a piece of shaped feces; from the rectum, shock-freeze in liquid nitrogen, store at −80° C.;

Human tumor tissue or precursors (aberrant crypts, adenomas, adenocarcinomas): biopsy during coloscopy or surgery.

b) Homogenization of fecal sample in buffer systems from commercial kits or in TE buffer (e.g. 10 mM Tris-HCl, pH 8.0, 1 mM EDTA), optionally using up to 400 mg/ml proteinase K; mix homogenate at 99° C. for 10 to 30 minutes, preferably 15 minutes, alternatively at 55° C. for 30 to 60 minutes, or at 37° C. for 30 to 60 minutes; centrifugation at 12,000 g for 5 minutes.

c) Isolation of DNA from supernatant of fecal sample homogenate or from tissue samples using commercial kits.

d) (optional:) Accumulation a. of target genes from total DNA by hybridizing sequence-specific biotinylated oligonucleotides with the target genes for APC, K-ras, β-catenin and B-raf, coupling the biotin residue to streptavidin, and separating via magnetic particles using commercial kits; the oligonucleotide sequences must be selected in such a way that the sequences hybridize with regions flanked by the primers subsequently used or situated close to the amplified section;

or b. of the neoplastic "long" DNA by excluding fragmented DNA with a size of <200 bp which is characteristic for DNA from apoptotic cells.

e) PCR with primers sequence-specific to selected regions in the genes for APC, K-ras, β-catenin and B-raf:

APC: primer pairs allow amplification of partially overlapping sequences in exon 15 within the region of frequently occurring mutations (mutational cluster region; MCR).

β-Catenin: primers on both sides of the MCR located in exon 3.

K-ras: primers on both sides of the frequently mutated codons 12 and 13 located in exon 1.

B-raf: primers located in exon 15, flanking the codons 593, 599 and 600.

All primers are selected in such a way that the PCR products have a size of from 180 to 350 bp.

f) Checkup of the PCR products on 2-3% agarose gel, preferably 2.5% agarose; optionally detection of deletions or insertions.

g) Purification of the PCR products using commercial kit.

h) Mutational analysis of the PCR products using suitable electrophoretic techniques, preferably SSCP: 5 to 14% acrylamide gel in 0.5 or 1×TBE buffer, preferably 8% acrylamide in 1×TBE; electrophoresis at 4 to 15° C., 300 mA, 2 to 4 hours, or 4° C., 100 mA, 16 hours.

Conventional staining methods, preferably silver nitrate staining.

Detection of conformation of single strands of samples compared to wild-type standard.

i) (optional:) DNA extraction from the SSCP gel and sequencing of DNA extracted from the SSCP gel, or of corresponding PCR products.

The invention claimed is:

1. In an improved method for the non-invasive early detection of colon cancer or intestinal cancer precursor cells in a sample by means of mutational analysis of two genes of each of two different signaling pathways, where the genes for the first pathway are APC, and β-catenin, and the genes for the second pathway are K-ras and B-raf, the improvement comprising using selected parts of the two genes in each of the signaling pathways which are combined for the analysis whereby the selection of the gene parts are determined by the following primer sequences and characterized in that where the method comprises the following steps:
   collecting a stool sample,
   homogenizing the sample,
   obtaining DNA from the sample,
   performing an amplification reaction in the genes for APC, K-ras, β-catenin and B-raf,
   using the following primers for APC:
   SEQ ID NO. 1,
   SEQ ID NO. 2, SEQ ID NO. 3,
SEQ ID NO. 4,
SEQ ID NO. 5,
SEQ ID NO. 6,
SEQ ID NO. 7,
SEQ ID NO. 8,
SEQ ID NO. 9,
SEQ ID NO. 10,
SEQ ID NO. 15,
SEQ ID NO. 16,
the following primers for K-ras:
SEQ ID NO. 11,
SEQ ID NO. 12,
the following primers for β-catenin:
SEQ ID NO. 13,
SEQ ID NO. 14,
and the following primers for B-raf:
SEQ ID NO. 17,
SEQ ID NO. 18,
wherein amplification products are formed, and
performing a mutational analysis in the amplification products to determine the existence of mutations in the APC, K-ras, β-catenin and B-raf genes.

2. The method according to claim 1, characterized in that the detection of mutations in selected sections of the genes for APC, K-ras, β-catenin and B-raf is effected by means of a DNA chip, said DNA chip including probes for APC, K-ras, β-catenin and B-raf from those regions of the above-mentioned genes that are flanked by the primer sequences specified in claim 1.

3. The method according to claim 1, characterized in that the APC, K-ras, β-catenin and B-raf genes are accumulated from total DNA by hybridizing sequence-specific biotinylated oligonucleotides with the genes for APC, K-ras, β-catenin and B-raf using coupling of the biotin residue to streptavidin and subsequent separation via magnetic particles.

4. The method according to claim 1, characterized in that amplification products, especially PCR products, are separated in an agarose gel for control purposes prior to purification.

5. The method according to claims 1, characterized in that the mutational analysis of the PCR products is effected using electrophoretic techniques, alternatively by means of a chromatographic procedure.

6. The method according to claim 5, characterized in that detected mutagenic conformations of a single strand are isolated and optionally sequenced.

7. The method of claim 5 where the electrophoretic techniques is SSCP.

8. The method of claim 5 where the chromatographic procedure is an HPLC-based procedure.

9. The method of claim 1 using the primers SEQ ID NO. 15 and SEQ ID NO. 10 for APC, the primers SEQ ID NO. 11 and SEQ ID NO. 12 for K-ras, the primers SEQ ID NO. 13 and SEQ ID NO. 14 for β-catenin, and the primers SEQ ID NO. 17 and SEQ ID NO. 18 for B-raf.

10. An improved kit, for the noninvasive early detection of colon cancer or intestinal cancer precursor cells in a sample by means of mutational analysis of two genes of each of two different signaling pathways, where the genes for the first pathway are APC, and β-catenin, and the genes for the second pathway are K-ras and B-raf, where the improved kit comprises selected parts of the two genes in each of the signaling pathways which are combined for the analysis where the selected gene parts are determined by the primer sequences from the group consisting of:
the following primers for APC:
SEQ ID NO. 1,
SEQ ID NO. 2,
SEQ ID NO. 3,
SEQ ID NO. 4,
SEQ ID NO. 5,
SEQ ID NO. 6,
SEQ ID NO. 7,
SEQ ID NO. 8,
SEQ ID NO. 9,
SEQ ID NO. 10,
SEQ ID NO. 15,
SEQ ID NO. 16,
the following primers for K-ras:
SEQ ID NO. 11,
SEQ ID NO. 12,
the following primers for β-catenin:
SEQ ID NO. 13,
SEQ ID NO. 14,
and the following primers for B-raf:
SEQ ID NO. 17,
SEQ ID NO. 18,
and information relating to combining the contents of the kit and for performing a mutational analysis according to claim 1 to determine the existence of mutations in the APC, K-ras, β-catenin and B-raf genes.

11. A method for the detection of colon cancer or colon cancer precursor cells using the kit according to claim 10 in the method of claim 1.

* * * * *

UNITED STATES PATENT AND TRADEMARK OFFICE
CERTIFICATE OF CORRECTION

PATENT NO.           : 7,833,757 B2
APPLICATION NO.      : 10/573134
DATED                : November 16, 2010
INVENTOR(S)          : Pablo Steinberg et al.

Page 1 of 1

It is certified that error appears in the above-identified patent and that said Letters Patent is hereby corrected as shown below:

Ttile page, Item [73], the Assignee

"universitael Posidam" should read

--Universitaet Potsdam--

Signed and Sealed this
Twenty-fifth Day of January, 2011

David J. Kappos
*Director of the United States Patent and Trademark Office*